United States Patent [19]
Fall et al.

[11] Patent Number: 5,849,970
[45] Date of Patent: Dec. 15, 1998

[54] MATERIALS AND METHODS FOR THE BACTERIAL PRODUCTION OF ISOPRENE

[75] Inventors: R. Ray Fall, Boulder, Colo.; Jennifer Kuzma, Woodbury, Minn.; Michele Nemecek-Marshall, Boulder, Colo.

[73] Assignee: The Regents of the University of Colorado, Boulder, Colo.

[21] Appl. No.: 493,978

[22] Filed: Jun. 23, 1995

[51] Int. Cl.⁶ .................................................. C07C 11/18
[52] U.S. Cl. ............................... 585/500; 585/1; 585/16; 585/500
[58] Field of Search ................................. 585/1, 16, 506, 585/500

[56] References Cited

PUBLICATIONS

Arlie, J.P. (1992) "Polyisoprene" Synthetic Rubbers, Processes and Economic Data, pp. 37–44, no month available.
Berenguer, J.A. et al. (1991) "Spoilage of a bakery product by isoprene–producing molds" Rev. Agroquim. Tecnol. Aliment. 31(4):580–583, no month available, Considered to the extend discussed in the specification.
Caillueax, J.A. et al. (1992) "Blood Isoprene Concentrations in Humans and in Some Animal Species" Biochemical Medicine and Metbolic Biology 47:157–160, no month available.
Davis, J.B., R.M. Squires "Detection of Microbially Produced Gaseous Hydrocarbons Other than Methane" Science 119:381–382, (Mar. 1954).
De Meester, C. et al. (1981) "Mutagenic Activity of Butadiene, Hexachlorobutadiene and Isopene" Industrial and Environmental Xenobiotics, pp. 195–203, No month available.
Fugii, T. et al. (1989) "The Relationship between Isobutene––Forming Activity and a Cytochrome P–450 in *Rhodotorula minuta*" Journal of Fermentation and Bioengineering 68(3):174–177, No month available.
Fujii, T. et al. (1987) "Isobutene production by *Rhodotorula minuta*" Appl. Microbiol. Biotechnol. 25:430–433, No month available.
Fukuda, H. et al. (1984) "Microbial Production of $C_3$– and $C_4$–Hydrocarbon under Aerobic Conditions" Agric. Biol. Chem. 48(6):1679–1682. No month available.
Gelmont, D. et al. "Isoprene—The Main Hydrocarbon in Human Breath" Biochemical and Biophysical Research Communications 99(4):1456–1460, (Apr. 1981).
Ince, J.E., C.J. Knowles (1986) "Ethylene formation by cell–free extracts of *Escherichia coli*" Arch. Microbiol 146:151–158, No month available.
Krone, U.E. et al. (1989) "Coenzyme $F_{430}$ as a Possible Catalyst for the Reductive Dehalogenation of Chlorinated $C_1$ Hydrocarbons in Methanogenic Bacteria" Biochemistry 28:10061–10065, No month available.
Kuzma, J., R. Fall (1993) "Leaf Isoprene Emission Rate is Dependent on Leaf Development and the Level of Isoprene Synthase" Plant Physiol. 101:435–440, No month available.
Kuzma, J., R. Fall "Bacteria Produce the Volatile Hydrocarbon Isoprene" 7th International Symposium on the Genetics of Industrial Microorganisms, abstract p.248, p. 179, (Jun. 26, 1994).
Kuzma, J.et al. "Bacteria Produce the Volatile Hydrocarbon Isoprene" Current Microbiology 30:97–103, (Feb. 1995).
Mark, H.F. et al. (1967) "Isoprene Polymers" Encyclopedia of Polymer Science and Technology 7:782–855, no month available.
Milne, P.J. et al. (1995) "Measurement of vertical distribution of isoprene in surface seawater, its chemical fate, and its emission from several phytoplankton monocultures" Marine Chemistry 48:237–244, no month available.
Monson, R.K., R. Fall (1989) "Isoprene Emission from Aspen Leaves" Plant Physiol. 90:267–274, no month available.
Monson, R.K. et al. (1992) "Relationships among Isoprene Emission Rate, Photosynthesis, and Isoprene Synthase Activity as Influenced by Temperature" Plant Physiol. 98:1175–1180, no month available.
Moore, R.M. et al. "Production of isoprene by marine phytoplankton cultures" Geophysical Research Letters 21(23):2507–2510, (Nov. 1994).
Ouchi, K. et al. (1980) "Regulation of Isoamyl Alcohol Formation via Ehrlich Pathway in *Saccaromyces cerevisiae*" J. Ferment. Technol. 58:301–309, no month available.

(List continued on next page.)

*Primary Examiner*—Elizabeth D. Wood
*Attorney, Agent, or Firm*—Saliwanchik, Lloyd & Saliwanchik

[57] ABSTRACT

A process for the bacterial production of the hydrocarbon isoprene (2-methyl-1,3-butadiene) is described and claimed. Various bacterial species, both Gram-negative and Gram-positive, were found to produce isoprene, and a method to isolate isoprene-producing bacteria from natural sources is described. Production of isoprene is confirmed by gas chromatography and gas chromatography-mass spectrometry. Of the tested species, Bacillus produces the most isoprene. Growth in a variety of media, including a chemically defined salts medium, in the presence of amino acid sources (casein, gelatin, or lactalbumin hydrolysates) supports isoprene production in logarithmic phase of growth, and with Bacillus cultured in a stirred fermentor, isoprene production occurs both in growing and non-growing cells. High isoprene production rates can also be restored to nutrient-limited cells by adding fresh media, suggesting isoprene production is dependent on nutrient availability. Isoprene can be produced under aerobic or anaerobic growth conditions. Temperature profiles for bacterial isoprene production show optima of 40°–60° C. that are suggestive of an enzymatic mechanism for isoprene formation; use of the thermophile *Bacillus stearothermophilus* allows more rapid bacterial growth and isoprene production at high temperature (e.g., 60° C.). Isoprene produced by bacteria, in contrast to petroleum-based isoprene, is essentially a pure hydrocarbon and can be harvested as a valuable feedstock for the manufacture of synthetic isoprene-based rubber and elastomers.

18 Claims, 8 Drawing Sheets

OTHER PUBLICATIONS

Silver, G.M., R. Fall (1991) "Enzymatic Synthesis of Isoprene from Dimethylallyl Diphosphate in Aspen Leaf Extracts" Plant Physiol. 97:1588–1591, no month available.

Silver, G.M., R. Fall (1995) "Characterization of Aspen Isoprene Synthase, an /ennzyme Responsible for Leaf Isoprene Emission to the Atmosphere" The Journal of Biological Chemistry 270(22):13010–13016, no month available.

Smith, M.R., L. Baresi (1989) "Methane Estimation for Methanogenic and Methanotrophic Bacteria" Gases in Plant and Microbial Cells, pp. 275–308, no month available.

Wright, S.J.L. et al. (1991) "Isoamyl alcohol (3–methyl–1–butanol), a volatile anti–cyanobacterial and phytotoxic product of some Bacillus spp." Letters in Applied Microbiology 13:130–132, no month available.

MATERIALS AND METHODS FOR THE BACTERIAL PRODUCTION OF ISOPRENE

This invention was made with government support from the National Science Foundation grant numbers ATM-9007849, ATM-9312153, and EAR-9256339 and from the United States Environmental Protection Agency grant number R-819431-01-0. The government has certain rights in this invention.

BACKGROUND OF THE INVENTION

Isoprene is a five carbon hydrocarbon (2-methyl-1,3-butadiene), that is an industrial chemical and a natural compound produced in biological systems. Isoprene production in plants has been well-studied. Production in plants is sporadic, with little evolutionary pattern. Isoprene emitters and non-emitters often exist within the same plant genus. Many isoprene-producing plants emit 1% to 2% of their fixed carbon as isoprene (Monson et al, 1989). Isoprene production has been shown to be tightly linked to light, leaf development, and temperature (Monson et al, 1992). An isoprene-producing enzyme, isoprene synthase, has been discovered (Silver and Fall, 1991) and purified (Silver and Fall, 1995) and is believed to be responsible for the in vivo production of isoprene from whole leaves (Kuzma et al, 1993).

There is some evidence for the production of isoprene by other higher organisms, including humans. Isoprene is a constituent of human breath (Gelmont et al, 1981), and has been detected in blood of humans and other animals (Cailleux et al, 1992). The role and mechanism of isoprene formation in mammals are unclear.

Many microorganisms, both prokaryotic and eukaryotic, produce one to four carbon volatile hydrocarbons such as methane, ethylene, propane, and isobutene (Davis et al, 1954; Fukuda et al, 1984; Fujii et at, 1987; Smith et al, 1989). The biochemical mechanisms of many of these emissions have been investigated (Fujii et al, 1989; Ince et al, 1986; Krone et al, 1989; Smith et al, 1989, supra). A five carbon volatile hydrocarbon, isoamyl alcohol (3-methyl-1-butanol), has been detected in cultures of Bacillus species and the yeast, *Saccharomyces cerevisiae* (Ouchi et al, 1980; Wright et al, 1991).

A few reports of microbial isoprene production have appeared. They include isoprene production by the fungus, *Eurotium amstelodami* (Berenguer et al, 1991), and detection of isoprene in marine phytoplankton cultures (Moore et al, 1994; Milne et al, 1995). The bacterial production of isoprene, described in detail here, has recently been published (Kuzma and Fall, 1994; Kuzma et aL, 1995).

Isoprene is an important chemical feedstock used in the synthetic rubber industry. About 800,000 tons per year of cis-polyisoprene are produced from the polymerization of isoprene; most of this polyisoprene is used in the tire and rubber industry (Arlie, 1992). Polyisoprene is also a copolymer used for the production of synthetic elastomers in other applications such as footwear, mechanical, medical, sporting goods, latex, and various industrial applications (Mark et al, 1967).

Currently, the tire and rubber industry is based on the use of natural and synthetic rubber. Natural rubber is obtained from the milky juice of rubber trees or plants found in the rainforests of Africa. Synthetic rubber is based primarily on butadiene polymers; butadiene is obtained as a co-product from ethylene and propylene manufacture.

It would be desirable to manufacture more synthetic rubber based on isoprene; to do this, an inexpensive supply of pure isoprene is needed. While isoprene can be obtained by fractionation of petroleum, the purification of this material is expensive and time-consuming. Petroleum cracking of the C5 stream of hydrocarbons produces only about 15% isoprene. An efficient, large scale, bacterial isoprene production process could provide an isoprene feedstock for synthetic isoprene-based rubber and provide a desirable, low-cost alternative to using natural rubber which can only be obtained by depleting a precious resource. Isoprene, which is a natural product and found in human breath (Cailleux et al, 1992, supra), is significantly less mutagenic than butadiene (De Meester et al, 1981). For this reason, it may be advantageous to use biologically produced isoprene for synthetic rubber and elastomer synthesis.

BRIEF SUMMARY OF THE INVENTION

The subject invention concerns the discovery that bacteria produce isoprene in significant quantities. Thus, one aspect of the subject invention is the use of bacteria in a process for producing isoprene.

The microbial production of isoprene according to the methods of the subject invention is particularly advantageous because isoprene produced by bacteria is essentially pure, in contrast to the isoprene produced by fractionating petroleum which is contaminated with products from incomplete cracking.

A further embodiment of the subject invention pertains to the advantageous use of media with nutrients including amino acids to grow the isoprene-producing bacteria. Bacteria grown in these media give enhanced yields of isoprene monomers which may be used in the production of synthetic rubber.

BRIEF DESCRIPTION OF THE DRAWINGS

FIG. 2A shows GC-MS run in total ion scanning mode. FIG. 2B shows the mass spectrum of the 16.51 minute peak (background subtracted).

FIG. 4A shows isoprene production vs. $Log_{10}$ number of cells FIG. 4B shows Time vs. $Log_{10}$ number of cells; typical growth curve. FIG. 4C shows the effect of adding fresh LB medium to cultures at an $A_{600}$ of 5.0.

-●- Isoprene production in cultures resuspended in fresh media.

-■- Isoprene production in cultures maintained in their old growth media.

Figure 5:
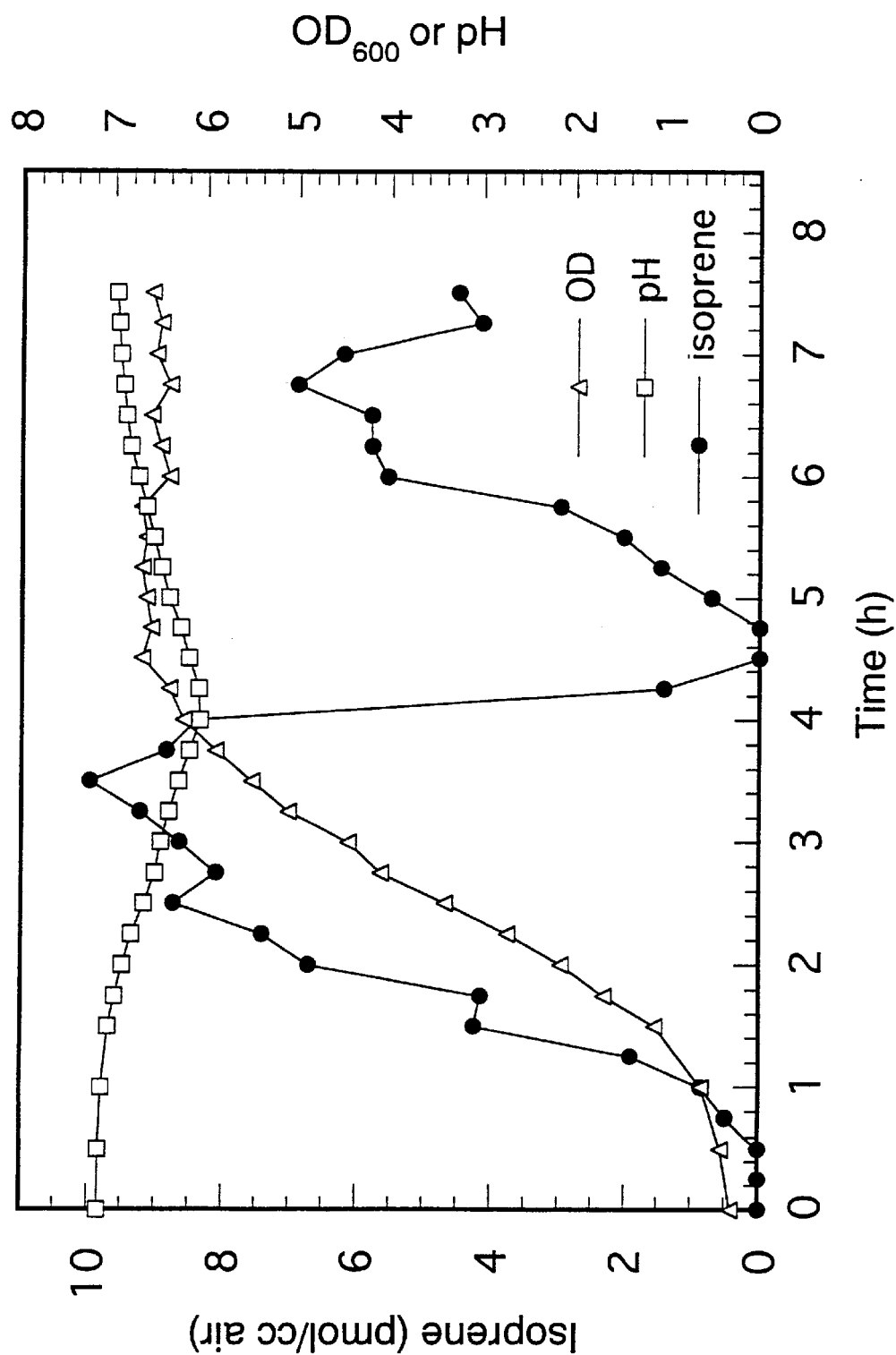

FIG. 5. Production of isoprene in a stirred fermentor using *B. subtilis* 6051. *B. subtilis* 6051 was inoculated into 1 liter of defined medium F containing 2% tryptone and 1% glucose and grown with aeration (2 liters oxygen per minute) in a 1.5 liter fermentor jar at 37° C. with stirring at 400 rpm. Isoprene production was sampled in the air stream exiting the fermentor. During growth the culture pH and optical density (600 nm) were monitored.

Figure 6A:
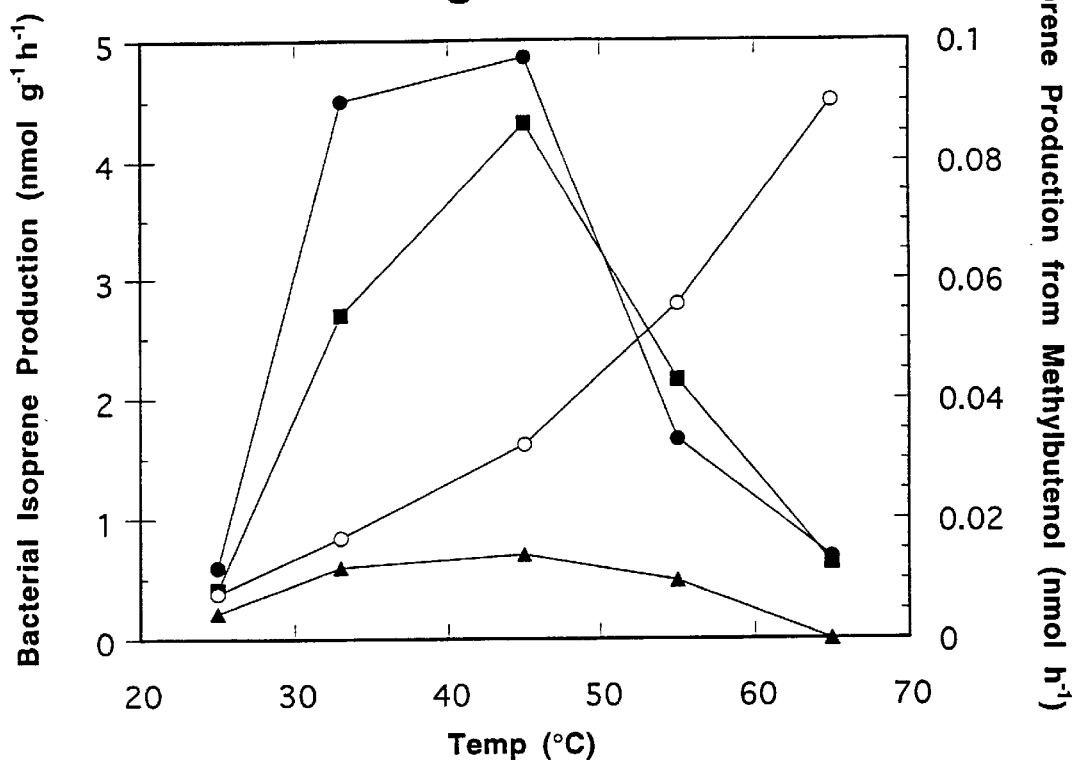
Figure 6B:
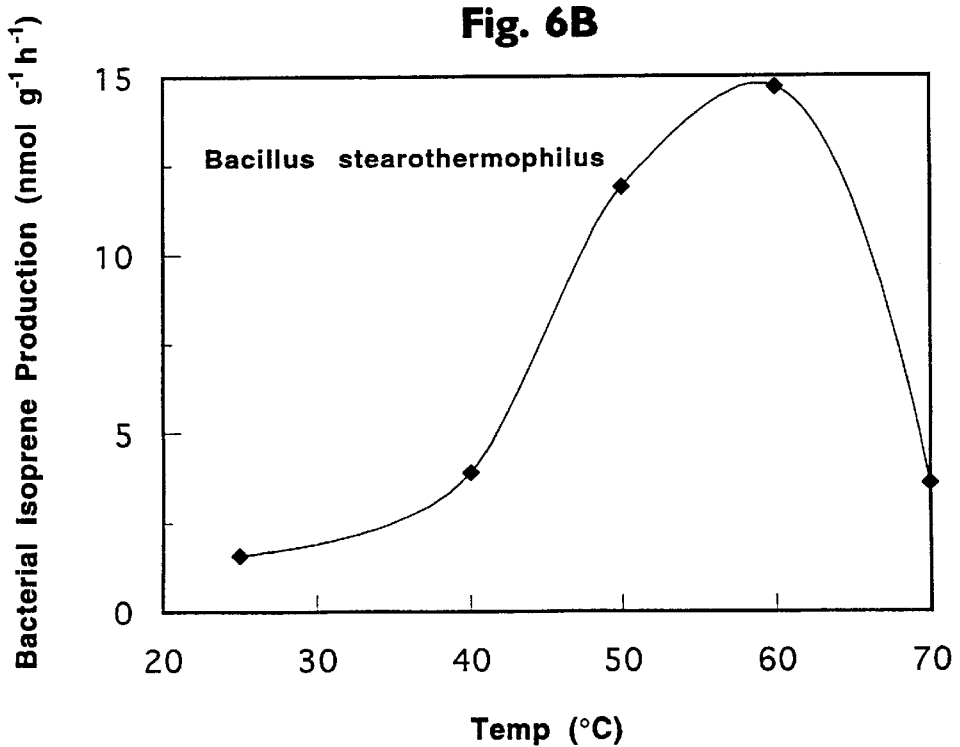

FIGS. 6A and 6B. Effect of temperature on isoprene production by several bacteria (FIG. 6A) and a thermophilic bacterium (FIG. 6B). Isoprene production rates for bacterial samples are on the left-hand y axis. Isoprene production rates for non-enzymatic alcohol samples are on the right-hand y axis.

-▲- *E. coli* isoprene production.

-■- *B. subtilis* 6051 isoprene production.

-●- *B. amyloliquefaciens* isoprene production.

-○- Non-enzymatic isoprene production from 3-methyl-2-buten-1-ol.

-♦- *B. Stearothermophilus* isoprene production.

DETAILED DESCRIPTION OF THE INVENTION

The subject invention concerns bacterial production of isoprene. Bacteria, as used herein, refer to unicellular, prokaryotic microorganisms. Surprisingly, various bacterial species were found to produce this volatile hydrocarbon. Production of isoprene was confirmed by gas chromatography-mass spectroscopy (GC-MS).

The method of the subject invention comprises culturing isoprene-producing bacteria and collecting isoprene from the culture. The subject invention further pertains to the use of nutrient rich and semi-defined media as described herein to optimize isoprene-production. As described herein, media additives should be chosen that do not interfere with or effect the isoprene product. One skilled in the art, having the benefit of the teachings provided herein, would be able to determine the proper nutrient additives to optimize the growth of a particular microbe.

Isoprene can be produced according to the procedures of the subject invention using either Gram-positive and Gram-negative bacteria. In a preferred embodiment of the subject invention, Eubacteria are used for isoprene production. The bacteria used according to the subject invention can be strict aerobes such as Bacillus sp., *Acinetobacter calcoceticus*, and *Agrobacterium rhizogenes*. Of the species tested, Bacillus produced the most isoprene.

A further aspect of the subject invention is the discovery that log phase cells produce more isoprene than stationary phase cells. Thus, high isoprene emission rates can be restored to nutrient-limited cells by adding fresh media. Various individual amino acids were tested, but none were able to restore isoprene to levels found in rich media. In a preferred embodiment of the subject invention, bacterial isoprene production can be enhanced by including tryptone in the culture medium. The concentration of tryptone can be from about 0.1% to 5%, with similar effects on isoprene production.

Production of isoprene in a stirred fermentor by *Bacillus subtilis* 6051 was demonstrated. Our results illustrate (1) that bacterial production of isoprene can be carried out in a fermentor, emulating a commercial fermentation scale-up; (2) that peak isoprene production reached about 100 nmol $g^{-1}$ $hour^{-1}$, about 10 times higher than we report in our published paper with sealed cultures (Kuzma et al, 1995, supra); and (3) that isoprene can be recovered from the fermentor by simple condensation of the exit gases. We have also demonstrated that isoprene formation by *Bacillus subtilis* 6051 is supported by virtually any complex amino acid source (tryptones, peptones, etc.). One aspect of the subject invention is the development of a semi-defined medium for isoprene production.

The optimal temperature of isoprene production from several bacteria was found to be approximately 45° C. The temperature profile seen for bacterial isoprene emission has the characteristics of an enzymatic process, where with increasing temperature, rates increase to an optimum and decline thereafter due to enzyme denaturation. It does not resemble the non-enzymatic conversion of 3-methyl-2-buten-1-ol to isoprene. For the thermophilic bacterium, *Bacillus stearothermophilus*, the optimal temperature for isoprene formation was higher at about 60° C., suggestive of a more thermostable enzymatic process for isoprene formation.

Using the teachings provided herein, cultures of isoprene-producing bacteria can be scaled up into large fermentors by methods well-known in the art. Isoprene can be collected from the fermentation by means well known in the art, including, for example, the simple condensation of the exit gas from the fermentation. Isoprene collected this way can be used as a monomer for rubber polymer synthesis, for elastomer synthesis, or for chemical feedstock.

Materials and Methods

Chemicals. Isoprene, 3-methyl-2-buten-1-ol, and 1,3-pentadiene were obtained from Aldrich Chemical Co., Inc. (Milwaukee, Wis.). Amino acids were obtained from Sigma Chemical Co. (St. Louis, Mo.). All other materials were reagent grade.

Organisms. Bacteria obtained from the American Type Culture Collection (ATCC) (American Type Culture Collection, 12301 Parklawn Drive, Rockville, Md. 20852) included the following: *Acinetobacter calcoaceticus* 23055, *Agrobacterium rhizogenes* 15834, *Bacillus amyloliquefaciens* 23842, *Bacillus subtilis* 6051, *Bacillus subtilis* 23059, *Bacillus subtilis* 23856, *Escherichia coli* 33694, *Streptomyces albus* 3004, *Streptomyces griseus* 10137, and *Pseudomonas citronellolis* 13674. Bacteria obtained from Carolina Biological Supply Company (P.O. Box 187, Gladstone, Oreg. 97027) included the following: *Bacillus cereus* 15-4870A, *Micrococcus luteus* 15-1575A, and *Rhodococcus rhodochrous* 15-5175. *Pseudomonas aeruginosa* JC9006 (Pemberton et al., 1973) and *Erwinia herbicola* M1 (Phelps et al 1986) are described in previous publications. *Bacillus cereus* 6A1, *Bacillus licheniformis* 5A24, *Bacillus megaterium* 7A2, and *Bacillus stearothermophilis* 9A1 were obtained from the Bacillus Genetic Stock Center (Ohio State University, 484 W. 12th Avenue, Columbus, Ohio 432.10).

Media. Several growth media were used: Luria-Bertani medium (LB), modified Schaeffer's sporulation medium (2×SG), M9 minimal glucose medium (M9) (all three are described in Harwood and Archibald, 1990), and M9 minimal glucose medium to which 1% Bacto-tryptone was added (M9T). For growth of the thermophile, *Bacillus stearothennophilus* 9A1, BST medium was used (Harwood and Archibald, 1990, supra). In addition, a defined medium (F) was developed for fermentor growth of Bacillus strains minimizing the production of volatile sulfur gases. Medium F, modified from Spizizen's minimal salts to reduce salt to half-strength, reduce available sulfate and include missing trace elements (Harwood and Archibald, 1990, supra), contains (per liter): 9.2 g $K_2HPO_4$(3 $H_2O$), 3 g $KH_2PO_4$, 1 g $NH_4Cl$, 500 mg trisodium citrate, 100 mg $MgSO_4$ (7 $H_2O$), 13.5 mg $FeCl_2$ (6 $H_2O$), 5.5 mg $CaCl_2$, 1.7 mg $ZnCl_2$, 1.0 mg $MnCl_2$ (4 $H_2O$), 0.6 mg $CoCl_2$ (6 $H_2O$), 0.6 $Na_2MoO_4$ (2 $H_2O$), and 0.43 mg $CuCl_2$ (2 $H_2O$). Medium F was routinely supplemented with 2% Bacto-tryptone and 1% glucose for fermentor growth; in some experiments Bacto-tryptone was replaced with 1% (w/v) of casamino acids (Difco), vitamin-free vitamin-free casamino acids (Difco), Gelysate peptone (BBL), lactalbumin hydrolysate (Oxoid) or HyCase SF (Sheffield Chemical). Cultures were maintained on TYG plates (5 g of tryptone, 2 g yeast extract, 25 g of glycerol, 12 g agar per liter). Yeast extract, Bacto-tryptone, nutrient broth, and agar used in the above media were obtained from Difco Laboratories (Detroit, Mich.).

Following are examples which illustrate procedures, including the best mode, for practicing the invention. These examples should not be construed as limiting. All percentages are by weight and all solvent mixture proportions are by volume unless otherwise noted.

EXAMPLE 1

Method for Isolating Isoprene-Producing Bacteria

With the benefit of the teachings provided herein, isoprene-producing bacteria can be easily isolated from soil, seawater, or other sources rich in bacteria. Bacterial colonies are enumerated and enriched on a suitable growth medium in petri dishes solidified with agar by standard techniques (Collins et al, 1989). Such agar plates with visible colonies can then be sealed with paraffin film for a suitable period of time (typically 1 to 4 hours), and the headspace of the plate can be sampled with a gas-tight syringe and analyzed for isoprene with a suitable gas chromatograph (Kuzma et al, 1995, supra). It is especially easy to obtain isoprene-producing Bacillus isolates from soil, water, food, etc. since these bacteria form heat-stable spores (Slepecky, 1992); samples can be heated at 80° C. (15 minutes) to kill vegetative cells, spores germinated on nutrient agar, and then isoprene-producing isolates can be identified by the above method.

EXAMPLE 2

Production and Identification of Isoprene

Figure 1:
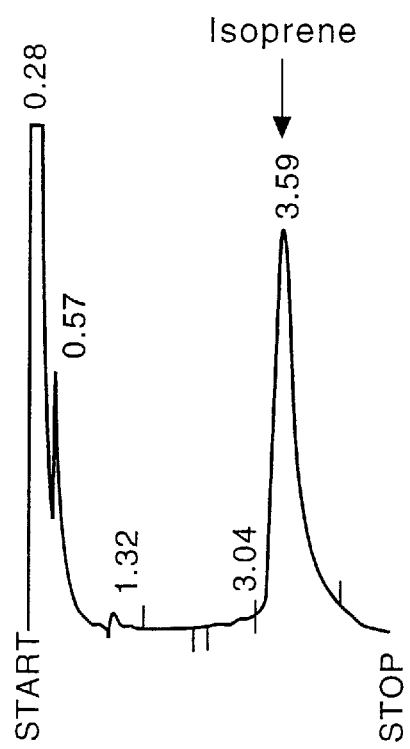
FIG. 1. A typical chromatogram showing isoprene in bacterial headspace. Two milliliters of headspace from a *B. subtilis* 6051 culture grown in M9 were analyzed by GC as described in Materials and Methods. Retention times are listed at the top of two peaks. Isoprene eluted at 3.59±0.05 minutes.

*E. coli, B. amyloliquefaciens, B. subtilis* 6051, and *A. calcoaceticus* were inoculated into 10 ml LB and grown for 16 hours at 32° C. with shaking (200 rpm) to an $A_{600}$ of approximately 1.5. For each strain, 2 ml of culture were incubated in 4 ml glass vials sealed with Teflon-lined septa for approximately 6 hours. Two ml of headspace were injected into a nickel trap cooled with liquid argon (-186° C.). The trap was subsequently heated to 150° C. with silica beads. At this time, the sample was injected onto a DB-1 column (30 m long, 1 µdiameter) (J&W Scientific, Folsom, Calif.) in a model 5890 Hewlett Packard gas chromatograph connected to a 5971A Hewlett Packard mass selective detector (electron ionization, operated in total ion mode). The temperature program for each GC-MS run included a 1 minute hold at -65° C. followed by a warming rate of 4° C. per minute. Helium carrier gas and a flow rate of approximately 0.7 ml/minute were used. This system is known in the art and described in more detail elsewhere (Cicerone et al, 1988). For the positive identification of bacterial isoprene production, peak retention time and mass spectra obtained from bacterial headspace were compared to the retention time and mass spectrum of an authentic isoprene standard. A typical gas chromatogram of headspace gases from a bacterial culture is shown in FIG. 1. Isoprene eluted at 3.6 minutes based on comparison to a high purity isoprene standard. The headspace of uninoculated LB medium was run as a negative control.

Figure 2A:
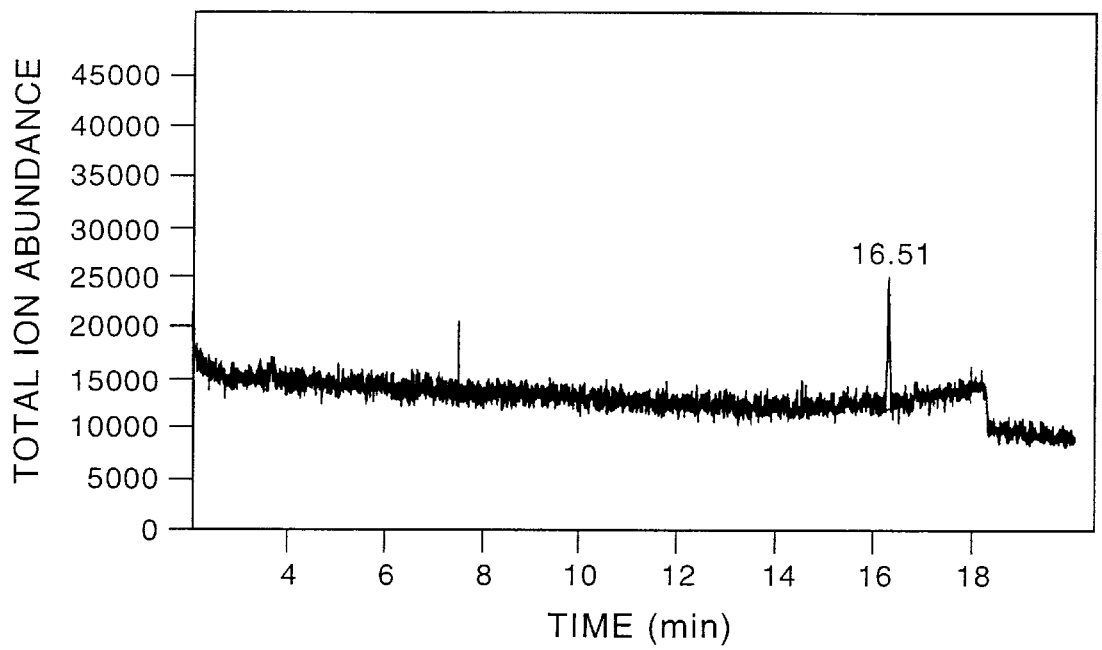
FIGS. 2A and 2B. Gas chromatography-mass spectroscopy (GC-MS) confirmation of *B. subtilis* 6051 isoprene production in LB medium.
Figure 2B:
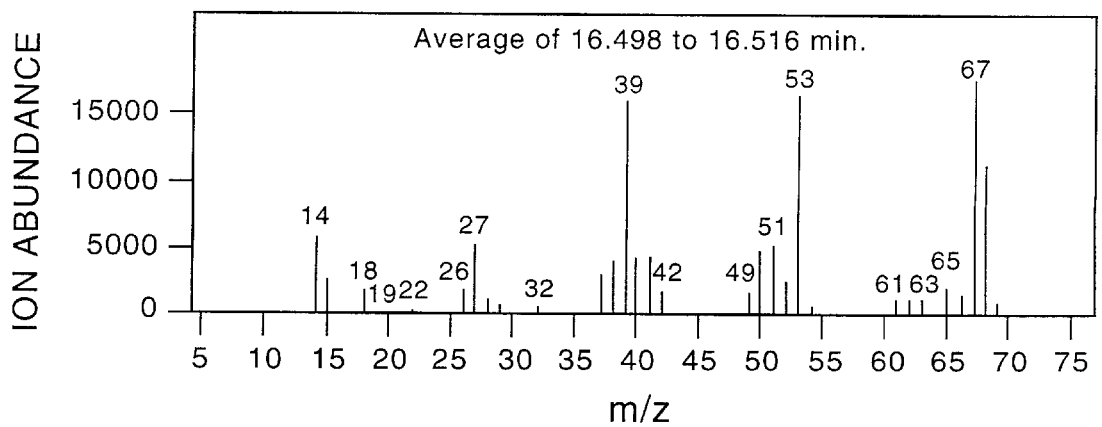

Isoprene production by *B. subtilis* 6051 cultures (FIGS. 2A and 2B) and *B. amyloliquefaciens, E. coli,* and *A. calcoaceticus* cultures was verified by GC-MS. For *B. subtilis* 6051, no other peaks were detectable by GC-MS from 2.0 minutes to 20.0 minutes (sharp peak at 7.6 minutes is detector noise). All $C_3$ to $C_6$ non-oxygenated hydrocarbons should elute during this time. The retention time (16.47 minutes) and mass spectrum for an isoprene standard were virtually identical to the retention time (16.50 minutes) and mass spectra of isoprene from the four bacteria. 1,3-pentadiene could not be distinguished from isoprene by comparison of mass spectra alone; however, a 1,3-pentadiene standard was run, and retention times for its two isomers were 17.80 minutes and 18.60 minutes. *E. coli* and *A. calcoaceticus* produced low levels of isoprene (i.e., levels slightly above detector noise), whereas Bacillus cultures produced much higher levels of isoprene (FIGS. 2A and 2B).

EXAMPLE 3

Survey of Isoprene Production by Bacterial Strains

Strains were grown for 16 hours at 32° C. with shaking to an $A_{600}$ ranging from 1.0 to 4.0 in some or all of the following media: M9, M9T, 2×SG, and LB. Two ml of culture were incubated in sealed vials at 32° C. with shaking (200 rpm) for approximately 3 hours. Two ml of headspace were analyzed with a gas chromatography (GC) system that is highly sensitive to isoprene. This system was operated isothermally (85° C.) with an n-octane/porasil C column (Alltech Associates, Inc., Deerfield, Ill.) and was coupled to a RGD2 mercuric oxide reduction gas detector (Trace Analytical, Menlo Park, Calif.). A more detailed description of this system is provided elsewhere (Greenberg et al, 1993; Silver et aL, 1991, supra). Isoprene production rates (nmol $g^{-1} h^{-1}$) were calculated as follows: GC area units were converted to nmol isoprene via a standard isoprene concentration calibration curve; $A_{600}$ values for all samples were taken and converted to grams of cells (g) by obtaining wet weights for cell cultures with a known $A_{600}$.

All values represent an average of 2 to 5 separate experiments. Two ml of uninoculated media were tested for isoprene as negative controls.

Survey results are depicted in Table 1. In some cases (e.g., *Escherichia coli, Pseudomonas aenrginosa,* and *Erwinia herbicola* in M9T), a peak of 3.2 minutes interfered with a precise quantitation of isoprene (3.6 minutes). In these cases, injection of smaller amounts of sample allowed better separation of the two peaks. The 3.2 minute peak was tentatively identified as dimethyl sulfide by GC-MS. It is known that many bacteria emit dimethyl sulfide (Drotar et al,, 1987).

TABLE 1

Production of isoprene by various bacterial stains

| Bacterial Strain | Isoprene production after growth in various media[a] (nmol $g^{-1}h^{-1}(A_{600})$)[b] | | | |
|---|---|---|---|---|
|  | M9 | M9T | 2xSG | LB |
| Gram positive | | | | |
| Bacillus amyloliquefaciens[c] | 1.44 (1.0) | 6.48 (2.2) | 8.28 (1.2) | 12.78 (1.1) |
| Bacillus cereus | 0.54 (1.5) | 2.70 (4.0) | 4.14 (6.0) | 4.32 (4.5) |
| Bacillus subtilis 6051[c] | 0.82 (2.1) | 6.48 (2.3) | 5.40 (1.6) | 9.54 (1.5) |
| Bacillus subtilis 23059 | 0.41 (1.6) | 4.32 (2.3) | 5.04 (1.5) | 9.00 (1.4) |
| Bacillus subtilis 23856 | 0.79 (2.5) | 3.06 (2.1) | 5.22 (1.5) | 7.02 (1.S) |
| Micrococcus luteus | 0.54 (2.2) | 1.11 (3.2) | 0.61 (5.0) | 0.36 (4.5) |
| Rhococcus rhodochrous | ND[d] | ND[d] | ND[d] | 1.18 (1.0) |
| Gram-negative | | | | |
| Acinetobacter calcoaceticus[c] | ND[d] | 3.42 (1.5) | 1.44 (2.1) | 1.44 (1.3) |
| Agrobacterum rhizogenes | ND[d] | ND[d] | 1.26 (1.6) | 4.14 (0.8) |
| Escherichia coli[c] | ND[d] | 0.41 (4.7) | 0.00 (1.6) | 0.54 (1.6) |
| Erwinia herbicola | 0.00 (2.1) | 0.59 (3.8) | 0.29 (2.2) | 0.90 (1.9) |
| Pseudomonas aeruginosa | 0.27 (1.3) | 0.54 (3.8) | 0.13 (2.9) | 0.72 (1.8) |
| Pseudomonas citronellolis | 0.23 (1.9) | 0.36 (5.0) | 0.56 (5.0) | 1.15 (2.0) |

[a]Media, strains, and experimental conditions are described in Materials and Methods. The data are the average of duplicate determinations.
[b]$A_{600}$ values are listed in parentheses after the numerical value for isoprene production.
[c]Isoprene production for these strains was confirmed by GC-MS. Isoprene production for other strains was confirmed by GC retention time.
[d]ND, Not determined Of the bacteria screened, Bacillus species were generally the highest producers of isoprene in all media. Two to twenty times more isoprene was detected in Bacillus cultures than in cultures of the other species. Among the Bacillus species, B. amyloliquefaciens was the highest isoprene emitter. Of the non-Bacillus species, Acinetobacter calcoaceticus in M9T medium and Agrobacterium rhizogenes in LB medium produced isoprene at levels comparable to Bacillus in those media. Isoprene was also produced by Streptomyces albus and Streptomyces gliseus in a variety of growth media. Isoprene production was not correlated with either Gram-positive or Gram-negative organisms (Table 1).

In the experiment shown in Table 1, both rich and minimal media were used. LB, 2×SG, and M9T are considered rich media; whereas M9 is considered a minimal medium with glucose as the sole carbon source and ammonium chloride as the sole nitrogen source. With the exception of M. luteus, isoprene production in rich media is significantly higher than in minimal media. The addition of 1% tryptone (Difco Laboratories, Inc., Detroit, Mich.) to M9 resulted in two- to ten-fold increases in isoprene production for all strains tested.

Figure 3:
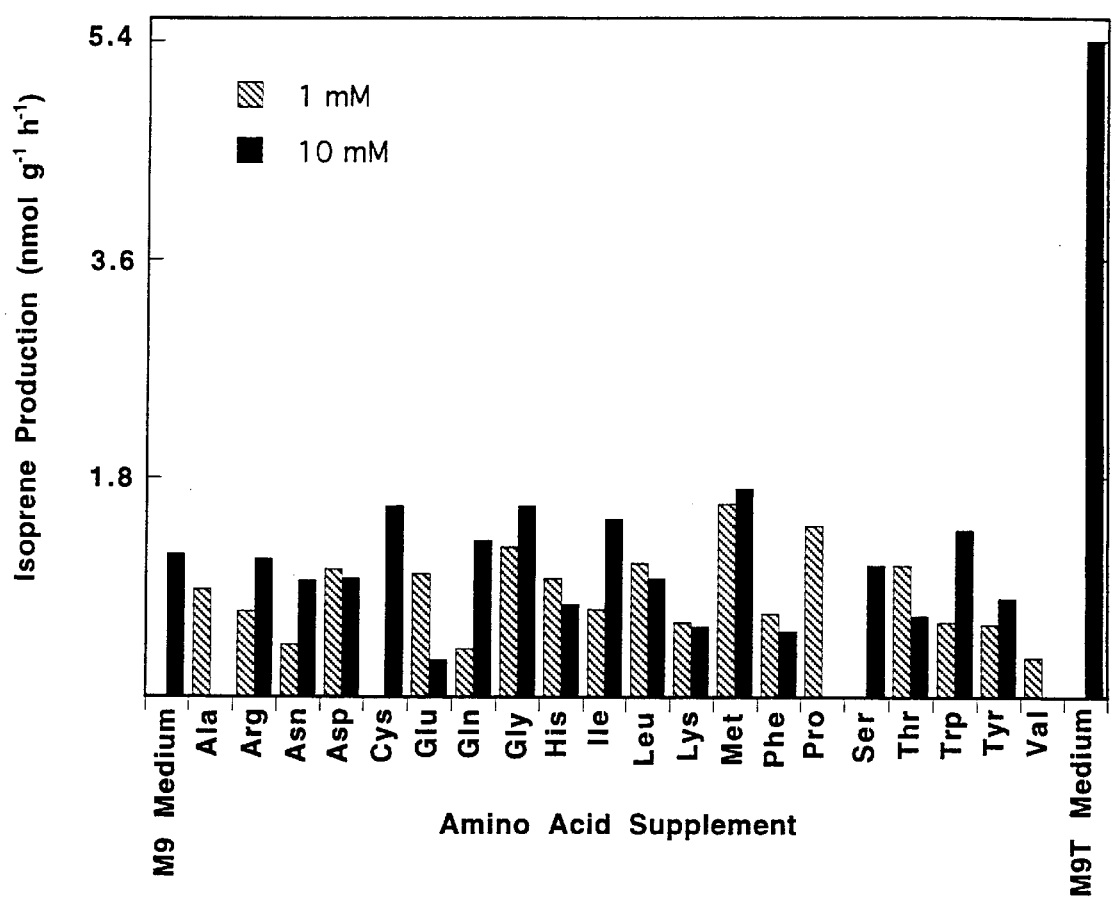
FIG. 3. Effect of amino acids on *B. subtilis* 6051 isoprene production. Individual amino acids were added to M9 minimal medium at concentrations of 1mM and 10 mM. For comparison, average emission rates for M9 (minimal medium without amino acids) and M9T (medium containing all amino acids, i.e., 1% tryptone) are shown on the far left and far right respectively (note that although legends for these controls are "10 mM=■", no amino acids have been added). 1 mM values for Ser and Cys and 10 mM values for Ala, Pro, and Val are not reported due to lack of bacterial growth in those cases.

To determine which amino acid components of the tryptone were responsible for stimulating isoprene production, B. subtilis 6051 was grown in minimal medium in the presence and absence of amino acids, and isoprene emissions rates were measured (FIG. 3). Amino acid addition experiments were performed as above with the addition of 1 mM and 10 mM L-amino acids to M9 medium from concentrated stock solutions. For 1 mM experiments, serine and cysteine were not tested due to lack of growth in the media. For 10 mM experiments, alanine, prolne, and valine were not tested also due to lack of growth. None of the amino acids individually, whether at 1 mM or 10 mM, stimulated isoprene production to the levels seen in medium with tryptone.

Various mixed amino acid sources could substitute for tryptone in isoprene production by Bacillus subtilis 6051. For example, isoprene production was supported by casein hydrolysates, and hydrolysates of gelatin and lactalbumin, as shown in Table 2.

TABLE 2

Various amino acid sources support isoprene production in Bacillus subtilis 6051

| Amino Acid Source[a] | Growth ($OD_{600}$) | Isoprene Production (nmol $g^{-1}h^{-1}$)[b] |
|---|---|---|
| Casein | 1.08 | 31.9 |
| (Casamino Acids) | 1.75 | 49.5 |
| Casein (Vitamin-free Casamino Acids) | 1.02 | 43.4 |
|  | 1.73 | 49.6 |
| Casein | 2.1 | 39.1 |
| (salt-free HyCase) | 3.2 | 50.7 |
| Casein | 1.45 | 54.8 |
| (Bacto-Tryptone) | 3.4 | 45.2 |
| Gelatin | 1.25 | 23.9 |
| (Gelysate peptone) | 1.8 | 33.4 |
| Lactalbumin | 2.52 | 17.6 |
| (Lactalbumin hydrolysate) | 2.85 | 39.7 |

[a]Bacteria were grown in medium F with 0.2% (w/v) glucose and the listed amino acid sources at 1% (w/v) concentration.
[b]Isoprene production in sealed vials was analyzed at the growth stages indicated ($OD_{600}$)

EXAMPLE 4

Growth and Media Effects on Isoprene Production

B. subtdis 6051 was grown in LB medium with shaking (200 rpm) at 32° C. During the course of 30 hours, aliquots of 2 ml were taken from these growing cultures and placed in sealed vials. These vials were incubated with shaking for 3 hours at 32° C., and then 2 ml of headspace were analyzed for isoprene by GC. Subsequently, the $A_{600}$ of the vials were taken. At an $A_{600}$ of approximately 5, two 20 ml sample cultures were centrifuged (5000×g). One of the cell pellets was resuspended in its old growth medium (the 20 ml supernatant). In the other sample, the supernatant was removed and saved (see below: "old media"), and 20 ml of fresh LB medium were added to the cell pellet. Both 20 ml samples were then incubated at 32° C. with shaking. Over the course of 7 hours, 2 ml aliquots of these cultures were analyzed by GC for isoprene production. Two ml aliquots of "old media", collected above, were incubated in sealed vials and analyzed for isoprene by GC after a 3 hour incubation. Isoprene production rates (nmol $g^{-1}$ $h^{-1}$) were calculated as above. Reported values for isoprene production are averages of two experiments.

Figure 4A:
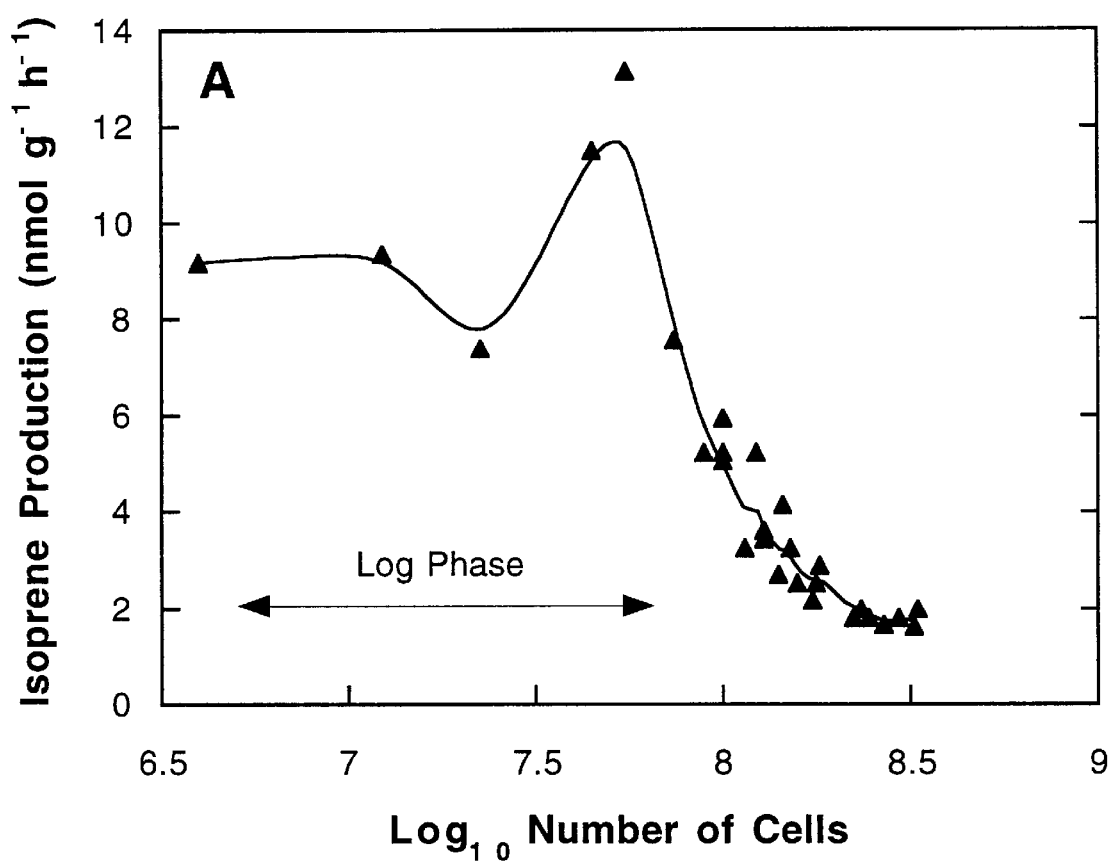
FIGS. 4A, 4B and 4C. Effect of growth stage and medium on isoprene production from *B. subtilis* 6051.
Figure 4B:
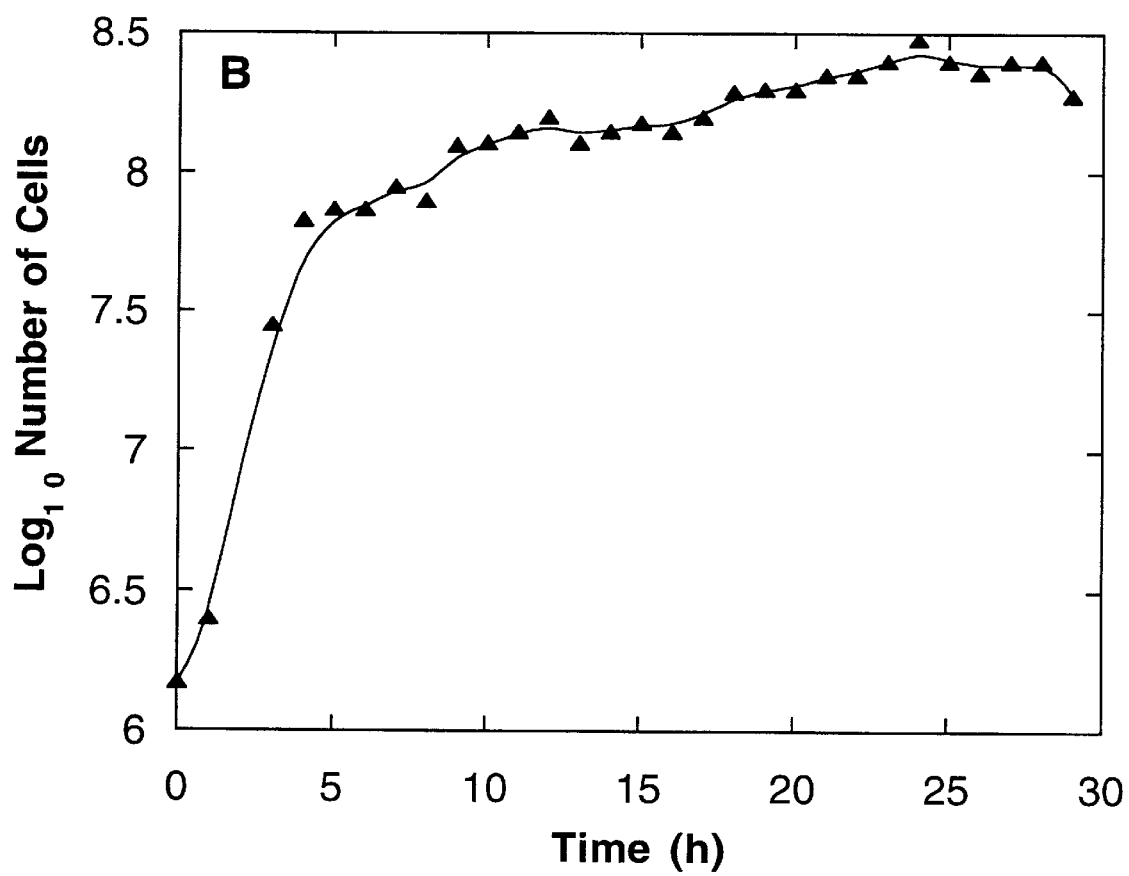

Isoprene showed an inverse relationship to $A_{600}$ in LB medium (FIG. 4A). The highest rates of isoprene production (8 to 12 nmol $g^{-1}$ $h^{-1}$) occurred during early growth (FIG. 4B,). In late logarithmic growth and stationary phase, isoprene production decreased to 2 nmol $g^{-1}$ $h^{-1}$.

Figure 4C:
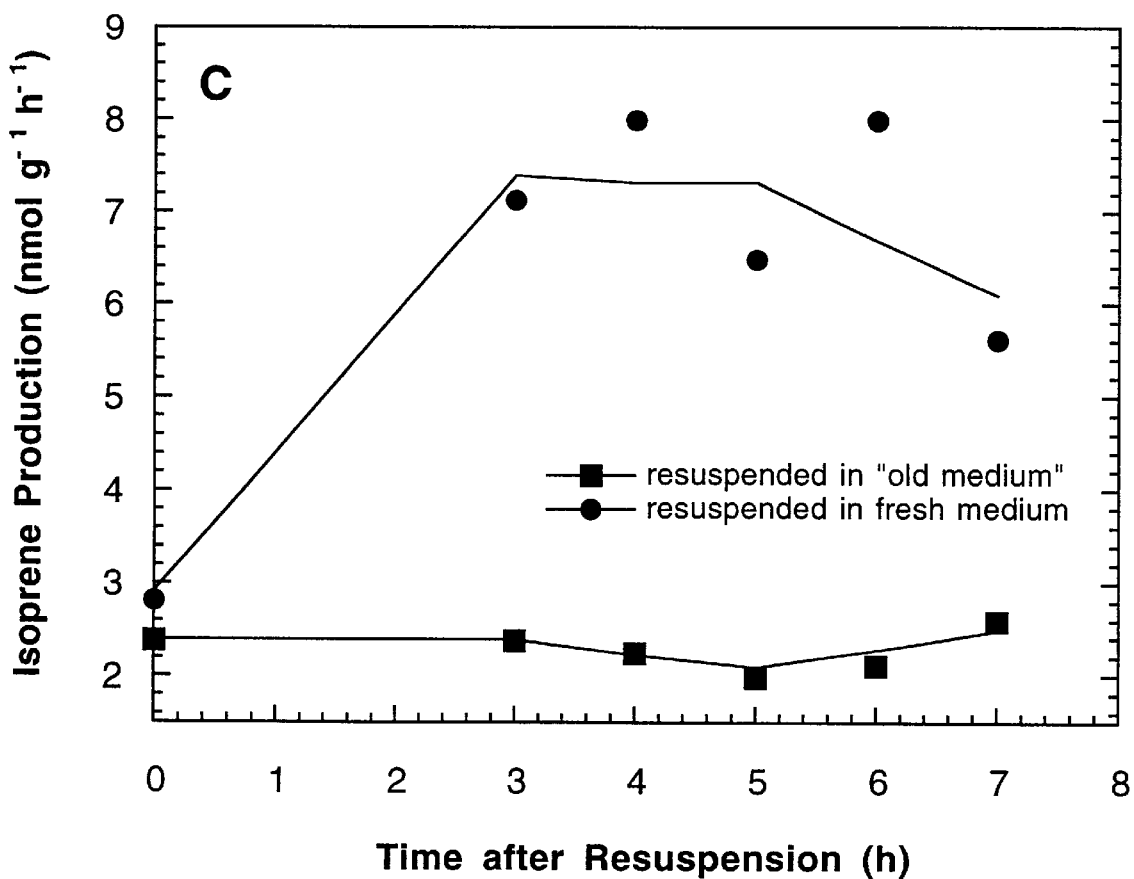

One hypothesis for this relationship between isoprene and growth phase is that nutrient depletion has a negative effect on the production of isoprene. To test this hypothesis, cultures of B. subtilis 6051 at an $A_{600}$ of approximately 5 and at an emission rate of 2 nmol $g^{-1}$ $h^{-1}$ were centrifuged, and the cells were resuspended in fresh LB medium (FIG. 4C). Control cultures were maintained in their old growth medium. Isoprene production rates for cells resuspended in fresh LB medium reached similar values to those of early growth cells. Rates for cells which were resuspended in their old growth medium resembled late growth or stationary phase cells.

EXAMPLE 5

Production of Isoprene in a Stirred Fermentor

When *Bacillus subilis* 6051 was grown in a stirred fermentor isoprene production was again maximal in late logarithmic phase, rapidly declining to zero in stationary phase; surprisingly, isoprene production resumed several hours later (FIG. 5). A similar result was seen in *Bacillus megatefium* 7A2. The reason for this biphasic production of isoprene is unknown.

EXAMPLE 6

Temperature Effects on Isoprene Production

*E. coli, B. subtilis* 6051, and *B. amyloliquefaciens* were grown in LB medium for 16 hours at 32° C. with shaking to an $A_{600}$ of approximately 1.0 to 3.0. Two ml aliquots of these cultures were incubated at various temperatures for 3 hours without shaking. For the non-enzymatic conversion of 3-methyl-2-buten-1-ol, 2 ml samples of LB were spiked with 5 nmol of the alcohol, and incubated at various temperatures. Two ml of headspace for bacterial and alcohol samples were analyzed for isoprene by GC. Reported values for isoprene production are averages of 2 experiments.

The optimal temperature for isoprene production by these bacteria is approximately 45° C. (FIG. 6A). The temperature profile seen for bacterial isoprene production has the characteristics of an enzymatic process, where with increasing temperature, rates increase to an optimum and decline thereafter due to enzyme denaturation. For the thermophilic bacterium, *Bacillus stearothermophilus*, which was grown at 60° C., the optimal temperature for isoprene formation was higher at about 50° C. to 60° C. (FIG. 6B). This result is consistent with a more thermostable enzymatic process for isoprene formation in this thermal-tolerant organism. In accordance with these findings, the bacteria can be grown according to the subject invention at temperatures ranging from about 25° C. to about 70° C., preferably about 40° C. to about 60° C.

EXAMPLE 7

Isoprene Production

Two experiments were conducted to confirm that the isoprene detected was produced by bacteria and was not a result of the production of isoprene precursors that were secreted by the bacteria into the medium and subsequently rearranged into isoprene.

The first experiment involved removing Bacillus cells from a grown culture and testing the resulting cell-free medium for isoprene production (see "old media" min Example 4). No significant quantities of isoprene were produced when aliquots of this "old media" were incubated alongside bacterial cultures.

Second, if a non-enzymatic conversion in the medium was responsible for isoprene production, this production should increase exponentially with temperature. In order to test this possibility, *B. subtilis* 6051, *B. amyloliquefaciens*, and *E. coli* in LB medium were incubated at various temperatures alongside a 3-methyl-2-buten-1-ol standard (FIG. 6A). Under acidic conditions 3-methyl-2-buten-1-ol rearragnes to isoprene at an appreciable non-enzymatic rate, and was therefore used as the non-enzymatic control. The conversion of the allylic alcohol to isoprene increased exponentially with increasing temperature. However, bacterial cultures exhibited a more complex temperature profile: a rise to approximately 45° C., followed by a decrease to almost zero isoprene production at 65° C. This profile suggests an enzymatic production of isoprene with denaturation of the enzyme at higher temperatures.

EXAMPLE 8

Anaerobic Production of Isoprene

To determine if bacteria grown anaerobically produce isoprene, two bacilli capable of anaerobic growth were tested. These bacteria, *Bacillus cereus* 6A1 and *Bacillus licheniformis* 5A24, were grown anaerobically in F medium supplemented with 2% Bacto-tryptone, 1% glucose, and 0.1% potassium nitrate. Isoprene production rates, determined as in Example 3, were as follows (averages of six determinations for each strain): *Bacillus cereus* 6A, 40.4 nmol isoprene $g^{-1}$ $h^{-1}$; and *Bacillus licheniformis* 5A24, 61.4 nmol isoprene $g^{-1}$ $h^{-1}$.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Arlie, J. P. (1992) "Polyisoprene," In *Synthetic Rubbers, Processes and Economic Data*, J. P. Arlie (ed.), Gulf Publishing Company, Houston, pp. 37–44.

Berenguer, J. A., V. Calderón, M. D. Herce, and J. J. Sánchez (1991) "Spoilage of a bakery product by isoprene-producing molds," *Rev. Agroquim. Tecnol Aliment.* 31:580–583.

Cailleux, A., M. Cogny, and P. Allain (1992) "Blood isoprene concentrations in humans and in some animal species," *Biochem. Med. Metabol. Biol.* 47:157–160.

Cicerone, R. J., L. E. Heidt, and W. H. Pollock (1988) "Measurements of atmospheric methyl bromide and bromoform," *J. Geophys. Res.* 93:3745–3749.

Collins, C. H., P. M. Lyne, and J. M. Grange (1989) *Collins and Lyne's Microbiological Methods*, 6th Ed., Butterworth-Heinemann, Oxford, pp. 407.

Davis, J. B., and R. M. Squires (1954) "Detection of microbially produced gaseous hydrocarbons other than methane," *Science* 119:381–382.

De Meester, C., M. Mercier, and F. Poncelet (1981) "Mutagenic activity of butadiene, hexachlorobutadiene, and isoprene," In: *Industrial and Environmental Xenobiotics*, I. Gut, M. Cikrt, and G. L. Plaa (eds.), Springer-Verlag, Berlin, p. 195–203.

Drotar A., G. A. Burton, J. E. Tavernier, and R. Fall (1987) "Widespread occurrence of bacterial thiol methyltransferases and the biogenic emission of methylated sulfur gas," *Appl. and Environ. Microbiol.* 53:1626–1631.

Fujii, T., T. Ogawa, and H. Fukuda (1989) "The relationship between isobutene-forming activity and a cytochrome P-450 in *Rhodotorula minuta*," *J. Ferment. Bioeng.* 68:174–177.

Fujii, T., T. Ogawa, and H. Fukuda (1987) "Isobutene production by *Rhodotorula minuta*," *Appl. Microbio. Biotechnol.* 25:430–433.

Fukuda, H., T. Fujii, and T. Ogawa (1984) "Microbial production of $C_3$- and $C_4$-hydrocarbons under aerobic conditions," *Agric. Biol. Chem.* 48:1679–1682.

Gelmont, D., R. A. Stein, J. F. Mead (1981) "Isoprene—the main hydrocarbon in human breath," *Biochem. and Biophys. Res. Comm.* 99:1456–1460.

Greenberg, J. P., P. R. Zimmerman, B. E. Taylor, G. M. Silver, and R. Fall (1993) "Sub-parts per billion detection of isoprene using a reduction gas detector with a portable gas chromatograph," *Atmos. Environ.* 27A:2689–2692.

Harwood, C. R., and A. R. Archibald (1990) "Growth, maintenance and general techniques," In *Molecular Biology Methods for Bacillus*, C. R. Harwood and S. M. Cutting (eds.), John Wiley & Sons, Chichester, p. 1–26.

Ince, J. E., and C. J. Knowles (1986) "Ethylene formation by cell-free extracts of *Escherichia coli.*," *Arch. Microbiol* 146:151–158.

Krone, U. E., K. Laufer, and R. K. Thauer (1989) "Coenzyme $F_{430}$ as a possible catalyst for the reductive dehalogenation of chlorinated $C_1$ hydrocarbons in methanogenic bacteria," *Biochemistry* 28:10061–10065.

Kuzma, J., and R. Fall (1993) "Leaf isoprene emission rate is dependent on leaf development and the level of isoprene synthase," *Plant Physiol.* 101:435–440.

Kuzma, J., and R. Fall (1994) "Bacteria produce the volatile hydrocarbon isoprene," 7th *International Symposium on the Genetics of Industrial Microorganisms*, Jun. 26–Jul. 1, 1994, Quebec, Canada, abstract p. 248.

Kuzma, J., M. Nemecek-Marshall, W. H. Pollock, and R. Fall (1995) "Bacteria produce the volatile hydrocarbon isoprene," *Curr. Microbiol.* 30:97–103.

Mark, H. F., N. G. Gaylord, and N. M. Bikales (eds.) (1967) "Isoprene polymers," In: *Encyclopedia of Polymer Science and Technology*, Vol. 7, Interscience Publishers, New York, p. 782–854.

Milne, P. J., D. D. Riemer, R. G. Zika, and L. E. Brand (1995) "Measurement of vertical distribution of isoprene in surface seawater, its chemical fate, and its emission from several phytoplankton monocultures," *Marine Chem.* 48:237–244.

Monson, R. K, and R. Fall (1989) "Isoprene emission from aspen leaves. Influence of environment and relation of photosynthesis and respiration," *Plant Physiol.* 90:267–274.

Monson, R. K., C. H. Jaeger, W. W. Adams, III., E. M. Driggers, G. M. Silver, and R. Fall (1992) "Relationships between isoprene emission rate, photosynthesis, and isoprene synthase activity as influenced by temperature," *Plant Physiol.* 98:1175–1180.

Moore, R. M., D. E. Oram, and S. A. Penkett (1994) "Production of isoprene by marine phytoplankton cultures," *Geophys. Res. Leters* 21:2507–2510.

Ouchi, K, Y. Yamamoto, M. Takagishi, and H. Akiyama (1980) "Regulation of isoamyl alcohol formation via Ehrlich pathway in *Saccharomyces cerevisiae*," *J. Ferment. Technol.* 58:301–309.

Pemberton, J. M., and A. J. Clark (1973) "Detection and characterization of plasmids in *Pseudomonas aeruginosa* strain PAO," *J. Bacteriology* 114:424–433.

Phelps, P., T. H. Giddings, M. Prochoda, and R. Fall (1986) "Release of cell-free ice nuclei by *Erwinia herbicola*," *Journal of Bacteriology* 167:496–502.

Silver, G. M., and R. Fall (1991) "Enzymatic synthesis of isoprene from dimethylallyl diphosphate in aspen leaf extracts," *Plant Physiol.* 97:1588–1591.

Silver, G. M., and R. Fall (1995) "Characterization of aspen isoprene synthase, an enzyme responsible for leaf isoprene emission to the atmosphere," *J. Biol. Chem.* 270:13010–13016.

Slepecky, R. A. (1992) "What is a Bacillus?" In: *Biology of Bacilli. Applications to Industry*, R. H. Doi and M. McGloughlin (eds.), Butterworth-Heinemann, Boston, p. 1–21.

Smith, M. R., and L. Baresi (1989) "Methane estimation for methanogenic and methanotrophic bacteria," In *Gases in Plant and Microbial Cells*, H. F. Linskens and J. F. Jackson (eds.), Springer-Verlag, Berlin.

Wright, S. J. L., C. J. Linton, R. A. Edwards, E. Drury (1991) "Isoamyl alcohol (3-methyl-1-butanol), a volatile anticyanobacterial and phytotoxic product of some Bacillus spp.," *Leters in Applied Microbiology* 13:130–132.

We claim:

1. A process for producing isoprene comprising the steps of culturing an isoprene-producing bacterium and recovering isoprene produced by the culture.

2. The process, according to claim 1, wherein said isoprene-producing bacterium is cultured under aerobic conditions.

3. The process, according to claim 1, wherein said isoprene-producing bacterium is cultured under anaerobic conditions.

4. The process, according to claim 1, wherein the isoprene-producing bacterium is cultured in nutrient-rich medium.

5. The process, according to claim 4, wherein said nutrient-rich medium is selected from the group consisting of Bacto-typtone, casamino acids, vitamin free casamino acids, Gelysate peptone and lactalbumin hydrolysate.

6. The process, according to claim 4, wherein said nutrient-rich medium comprises tryptone at about 0.1% to about 5% by weight.

7. The process, according to claim 1, wherein said isoprene-producing bacterium is cultured between about 25° C. and about 70° C.

8. The process, according to claim 7, wherein said isoprene-producing bacterium is cultured at about 40° C. and about 60° C.

9. The process, according to claim 7, wherein said isoprene-producing bacterium is thermophilic and cultured at temperatures above about 50° C.

10. The process, according to claim 1, wherein said isoprene-producing bacterium is selected from the group consisting of Acinetobacter, Agrobacterium, Bacillus, Erwinia, Escherichia, Micrococcus, Pseudomonas, Rhodococcus, and Streptomyces.

11. The process, according to claim 10, wherein said isoprene-producing bacterium is a Bacillus species.

12. The process, according to claim 11, wherein said Bacillus species is *Bacillus amyloliquefaciens* having the identifying characteristics of ATCC 23842.

13. The process, according to claim 10, wherein said isoprene-producing bacterium is *Acinetobacter calcoaceticus* having the identifying characteristics of ATCC 23055.

14. The process, according to claim 1, wherein said isoprene-producing bacterium is cultured in a fermentor.

15. The process, according to claim 14, wherein said isoprene is recovered from the exit gas of said fermentor.

16. The process, according to claim 15, wherein said isoprene is recovered from said exit gas by condensation.

17. The process, according to claim 1, wherein said bacteria are grown in a medium comprising

| Component | Quantity Per Liter |
| --- | --- |
| K$_2$HPO$_4$(3H$_2$O) | 9.2 g |
| KH$_2$PO$_4$ | 3 g |
| NH$_4$Cl | 1 g |
| trisodium citrate | 500 mg |
| MgSO$_4$ (7H$_2$O) | 100 mg |
| FeCl$_2$ (6H$_2$O) | 13.5 mg |
| CaCl$_2$ | 5.5 mg |
| ZnCl$_2$ | 1.7 mg |
| MnCl$_2$ (4H$_2$O) | 1.0 mg |
| CoCl$_2$ (6H$_2$O) | 0.6 mg |
| Na$_2$MoO$_4$(2H$_2$O) | 0.6 mg |
| CuCl$_2$(2H$_2$O) | 0.43 mg. |

18. The process, according to claim 17, wherein said medium further comprises about 2% by weight Bacto-tryptone and about 1% by weight glucose.

* * * * *

UNITED STATES PATENT AND TRADEMARK OFFICE
CERTIFICATE OF CORRECTION

PATENT NO. : 5,849,970

DATED : December 15, 1998

INVENTOR(S) : R. Ray Fall, Jennifer Kuzma, Michele Nemecek-Marshall

It is certified that error appears in the above-identified patent and that said Letters Patent is hereby corrected as shown below:

Column 1, line 50: "et aL," should read --et al.,--.

Column 2, line 60: "of cells FIG 4B shows" should read --of cells. FIG 4B shows--.

Column 4, lines 60-61: "stearothennophilus" should read --stearothermophilus--.

Column 5, line 4: "0.6 $Na_2MoO_4$," should read --0.6 mg $Na_2MoO_4$--;

lines 8-9: "vitamin-free vitamin-free casamino" should read --vitamin-free casamino--; and line 56: "1 $\mu$diameter)" should read --1 $\mu$m diameter)--.

Column 6, line 47: "et aL," should read --et al.,--; and line 59: "aenrginosa" should read --aeruginosa--.

Column 7, line 15: "7.02 (1.S)" should read --7.02 (1.5)--;

line 44: "gliseus" should read --griseus--; and line 66: "prolne" should read --proline--.

Column 8, line 35: "subtdis" should read --subtilis--.

Column 9, line 9: "subilis" should read --subtilis--;

line 14: "megatefium" should read --megaterium--; and line 57: "min" should read --in--.

UNITED STATES PATENT AND TRADEMARK OFFICE
CERTIFICATE OF CORRECTION

PATENT NO. : 5,849,970

DATED : December 15, 1998

INVENTOR(S) : R. Ray Fall, Jennifer Kuzma, Michele Nemecek-Marshall

It is certified that error appears in the above-identified patent and that said Letters Patent is hereby corrected as shown below:

Column 10, lines 36-37: "S ánchez" should read --Sánchez--;

line 66: "*Microbio.*" should read --*Microbiol.*--.

Column 11, line 52: "*leters*" should read --*Letters*--.

Column 12, line 14: "*Leters*" should read --*Letters*--; and

Column 12, line 40: "and about" should read --to about--.

Signed and Sealed this

Fifteenth Day of June, 1999

Q. TODD DICKINSON

Attest:

Attesting Officer

Acting Commissioner of Patents and Trademarks